US008653030B2

(12) United States Patent
Kohn et al.

(10) Patent No.: US 8,653,030 B2
(45) Date of Patent: Feb. 18, 2014

(54) PHARMACEUTICAL FORMULATION COMPOSED OF A POLYMER BLEND AND AN ACTIVE COMPOUND FOR TIME-CONTROLLED RELEASE

(75) Inventors: Joachim B. Kohn, Piscataway, NJ (US); Deborah M. Schachter, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1136 days.

(21) Appl. No.: 11/970,028

(22) Filed: Jan. 7, 2008

(65) Prior Publication Data

US 2008/0194469 A1 Aug. 14, 2008

Related U.S. Application Data (63) Continuation of application No. 10/169,350, filed as application No. PCT/US01/00045 on Jan. 2, 2001, now Pat. No. 7,326,425.

(60) Provisional application No. 60/174,133, filed on Dec. 31, 1999.

(51) Int. Cl.
*A61K 38/12* (2006.01)
*A61K 47/34* (2006.01)
*A61K 38/02* (2006.01)

(52) U.S. Cl.
USPC ............ 514/9; 514/772.3; 514/2; 514/772.1; 514/772.7

(58) Field of Classification Search
None
See application file for complete search history.

(56) References Cited

U.S. PATENT DOCUMENTS

| 5,198,507 | A | * | 3/1993 | Kohn et al. | .................... 525/432 |
| 5,670,602 | A | * | 9/1997 | Kohn et al. | .................... 528/176 |
| 5,877,224 | A | * | 3/1999 | Brocchini et al. | .......... 514/772.2 |
| 5,912,225 | A | * | 6/1999 | Mao et al. | .......................... 514/2 |

FOREIGN PATENT DOCUMENTS

| JP | 11510160 T | 9/1999 |
| WO | 9719996 A1 | 6/1997 |
| WO | 9836013 A1 | 8/1998 |
| WO | 9924107 A1 | 5/1999 |

OTHER PUBLICATIONS

Benzina et al., A versatile three-iodine molecular building block leading to new radiopaque polymeric biomaterials, Journal of Biomedical Materials Research, Nov. 1, 1996, pp. 459-466, vol. 32, John Wiley & Sons, Inc., US.

\* cited by examiner

*Primary Examiner* — Cecilia J Tsang
*Assistant Examiner* — Tara Martinez
(74) *Attorney, Agent, or Firm* — Fox Rothschild LLP (57) ABSTRACT

A formulation containing a biologically active compound having a chemical structure with hydrogen bonding sites, a first biocompatible, hydrolytically degrading polycarbonate with hydrogen bonding sites and tyrosine-derived diphenol monomer units, and a second biocompatible hydrolytically degrading polymer that is less hydrophobic than the polycarbonate, wherein the second polymer degrades hydrolytically to form acidic degradation products that promote the release of the active compound. Methods for active compound delivery are also disclosed.

15 Claims, 9 Drawing Sheets

FIG. 1 desaminoCys-homoArg-Gly-Asp-Trp-Pro-Cysamide

PHARMACEUTICAL FORMULATION COMPOSED OF A POLYMER BLEND AND AN ACTIVE COMPOUND FOR TIME-CONTROLLED RELEASE

CROSS-REFERENCE TO RELATED APPLICATIONS

The present application is a Continuation of U.S. application Ser. No. 10/169,350, which has a 35 U.S.C. §371 acceptance date of Dec. 23, 2002 and claims §371 priority of PCT/US01/00045 filed Jan. 2, 2001, which, in turn, claims priority benefit under 35 U.S.C. §119(e) of U.S. Provisional Patent Application Ser. No. 60/174,133 filed Dec. 31, 1999. The disclosures of all three applications are incorporated herein by reference.

BACKGROUND OF THE INVENTION

The literature is replete with examples of the delayed or pulsed release of active agents using polymeric materials. However, it is possible to divide these systems into two basic categories; those that depend on an environmental stimulus to induce release of the active agent from the polymeric matrix and those that are designed to release the drug after particular intervals of time have elapsed. Examples of environmental stimuli that have been used are electrical impulses, pH or temperature changes, application of magnetic fields, or ultrasound.

Those systems that are time-controlled can further be divided into those that use a barrier technology that is placed around the active agent that is designed to degrade or dissolve after a certain time interval, and those that use the degradation of the polymer itself to induce the release of the active agent.

One approach has been to prepare a polymeric hydrogel composed of derivitized dextran and to incorporate into the hydrogel, a model protein, $I_gG$, with an enzyme, endo-dextranase that degrades the hydrogel. It was observed that without the enzyme the release of the protein was very slow. However, when the enzyme was included in the formulation, the release rate was dependent on the concentration of the enzyme. At high concentrations, the release was fast and complete. At low concentrations, the release was delayed.

Delayed release in association with hydrolytic degradation of the polymer has also been investigated. Heller's so-called "$3^{rd}$ generation" poly(ortho esters) are viscous ointments at room temperature and when mixed with a model protein, lysozyme, demonstrated a delayed release profile. The length of the delay time was found to correlate with polymer molecular weight and alkyl substituent of the polymer.

Ivermectin, a water insoluble antiparasitic agent for veterinary applications, was encapsulated in PLGA (50:50) microspheres and the subsequent pulsed release of this agent, in vivo, was shown to be dependant on the degradation rate of the polymer matrix. Pulsed and delayed release of active agents from PLGA microspheres was most intensely studied by Cleland et al. The PLA or PLGA microspheres were processed using a high kinematic viscosity of polymer solution and a high ratio of polymer to aqueous solution. This produced dense microspheres, which required severe bulk erosion of the polymer to release the drug. These conditions yield microspheres that have low loading (generally 1% w/w), moderate bursts, and lag times during which significant leaching of drug occurs.

SUMMARY OF THE INVENTION

The technology described in this disclosure represents a departure from the prior art. In this system, bonding interactions between the polymer and the active compound are used to lock the active compound into the polymeric matrix. While one can envision several different types of interactions (adsorption, pi-bonding, ionic), hydrogen bonding interactions seem to be most suitable.

Therefore, according to one aspect of the present invention, a formulation containing a biologically active compound is provided having a structure with hydrogen bonding sites, blended with a first polymer having a structure with complementary hydrogen bonding sites, and a second polymer that degrades to form degradation products that promote the release of the active compound from the first polymer.

The formulation thus consists of three components, two polymers and a biologically active compound all blended together. The present invention thus provides new implantable or injectable drug release systems that release a pharmaceutically or biologically active compound in a time-controlled fashion, allowing the design of delay times prior to release, the design of pulsatile release, and the design of systems with high loadings that are resistant to "burst" (e.g., the immediate and uncontrolled release of a substantial amount of the loaded drug within a very short initial period of use).

The present invention uses the degradation products of one polymer to trigger the release of the active compound from the other polymer. In addition, the delayed release of the active compound can be achieved without the use of barrier systems that require complex and sophisticated formulation techniques. Further, the present invention relies on the formation of hydrogen-bonds between the active compound and the slow degrading, hydrophobic matrix polymer. This feature makes it possible to incorporate unexpectedly high loadings of water-soluble active compounds into the system without any burst (as defined above). Unlike the behavior that is observed when water-soluble peptides are incorporated into any of the commonly used alpha-hydroxy acid based polymers such as poly(lactic acid), poly(glycolic acid) or polydioxanone, in the system of the present invention, the formation of hydrogen-bond mediated interactions between the polymeric matrix and the active compound prevents burst, even at exceptionally high loadings.

There are many drugs that are more effective when given to the patient in a pulsatile manner as opposed to a continuous release fashion. For example, an area of great interest, currently, for this type of delivery system is single-shot immunization. Immunity is best induced by a pulsatile delivery of the antigen, hence the need for booster shots. It has been suggested that it would be more economical and effective, especially in third world countries, if a delivery system for antigens such as tetanus toxoid or gp120 (under development for an AIDS vaccine) could be implanted once into the patient and provide for the release of booster doses at preprogrammed time periods.

Therefore, the present invention also includes a method for the pulsatile delivery of a biologically active compound to a patient in need thereof by administering to the patient the formulation of the present invention.

This type of drug delivery is also important for hormonal based drug delivery. Fertility and birth control drug therapy for both animals and humans is not continuous, but rather cyclic in nature since these therapies work synergistically with the menstrual cycle and the corresponding hormonal flux. This is another direction in drug delivery in which delayed and/or pulsed release of an active compound would be applicable.

Agricultural applications which require the timed dosing of fertilizers, weed-killers, and other active agents is another area where this invention would be important.

DETAILED DESCRIPTION OF THE PREFERRED EMBODIMENTS

The first polymer in the blend is a slowly degrading, relatively hydrophobic and biocompatible polymer. In order to encourage the formation of hydrogen bonding interaction with the biologically active compound, it is also necessary to choose a highly functional polymer system as the first polymer. In its broadest embodiment, the slow degrading, hydrophobic, biocompatible polymer can be any such polymer that contains hydrogen-bonding sites as part of its chemical structure. In its most preferred embodiment, this slow degrading and hydrophobic polymer is selected from the tyrosine-derived polyarylate libraries disclosed in U.S. Pat. No. 5,216,115 and WO 99/52962, the disclosures of both of which are incorporated herein by reference. Members of this library all share the same highly functional structural template but are distinguished from one another by subtle structural changes. The functional groups of the main template provide sites for interactions. These are pi stacking of its aromatic rings with an aromatic ring of a peptide, or hydrogen bonding of the ✕-amido carboxylate region with a corresponding group in the peptide. The small structural variations between members allow the fine-tuning of these interactions to suit particular proteins or peptides.

Also preferred are any of the polymers that can be derived from the tyrosine-derived diphenol compounds of U.S. Pat. No. 5,587,507 and the tyrosine-derived dihydroxy monomers of WO 98/36013, the disclosures of both of which are also incorporated herein by reference. In addition to the above-referenced polyarylates, examples include the polycarbonates of U.S. Pat. No. 5,099,060, the polyiminocarbonates of U.S. Pat. No. 4,980,449, the polyphosphazenes and polyphosphates of U.S. Pat. No. 5,912,225, polyurethanes, including the polyurethanes of U.S. Pat. No. 5,242,997, the random poly(alkylene oxide) block copolymers of U.S. Pat. No. 5,658,995, and a wide range of other polymers that can be derived from the above-referenced tyrosine-derived diphenol compounds, the tyrosine-derived dihydroxy compounds and similar peptides. All of the above referenced patent publications are incorporated herein by reference. Notably, corresponding polymers of the tyrosine-derived dihydroxy compounds can be made by any of the processes of any of the above-referenced patents disclosing polymers of tyrosine-derived diphenol compounds.

Figure 1:
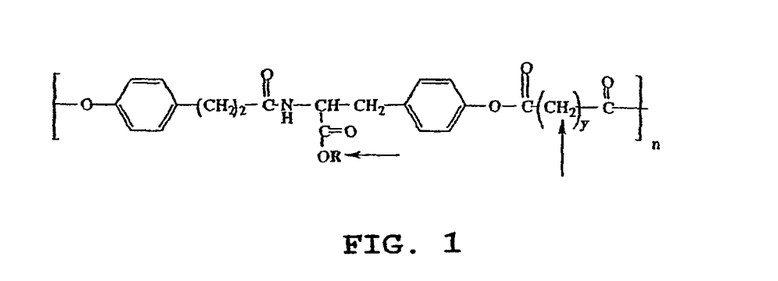
FIG. 1 depicts the chemical structure of a tyrosine-derived polyarylate, in which the arrows designate sites at which variations are introduced into the polymer.

A particularly preferred first polymer is the poly(desaminotyrosyltyrosine hexyl ester adipate (Poly(DTH adipate)) of FIG. 1 (y=4; R=hexyl). Poly(DTH adipate) having a weight-average molecular weight between about 80,000 and about 200,000 daltons is particularly preferred.

Any biologically active moiety with hydrogen-bonding sites that can be physically dispersed within the polymer blend can be used as a biologically active compound for release. Examples of hydrogen bonding sites include primary and secondary amines, hydroxyl groups, carboxylic acid and carboxylate groups, carbonyl (carboxyl) groups, and the like. While one can apply the current invention to any active compound that has hydrogen bonding sites, including natural and unnatural antibiotics, cytotoxic agents and oligonucleotides, amino acid derived drugs such as peptides and proteins seem to be most appropriate for this technology. The compositions of the present invention overcome some of the difficulties encountered in previous attempts to formulate controlled release devices that show reproducible release profiles without burst and/or lag effects. In its most preferred embodiment, the active compound is a peptide that is stable under mildly acidic conditions.

Peptide drugs suitable for formulation with the compositions of the present invention include natural and unnatural peptides, oligopeptides, cyclic peptides, library generated oligopeptides, polypeptides and proteins, as well as peptide mimetics and partly-peptides. Peptide drugs of particular interest include platelet aggregation inhibiting (PAI) peptides, which are antagonists of the cell surface glycoprotein Iib/IIIa, thus preventing platelet aggregation, and ultimately clot formation. Preferred PAI peptides include the PAI peptides disclosed by WO 90/15620, the disclosure of which is incorporated herein by reference, particularly INTEGRILIN™ (FIG. 2), a medically useful cyclic PAI heptapeptide.

In the case of peptide drugs, interactions between the peptide and the first polymer inhibit the release of the peptide. These interactions are composed of hydrogen bonding and hydrophobic forces. It has been discovered that these interactions can be weakened under conditions of low pH, resulting in the release of the peptide. Thus, one method of achieving this is to blend in a second polymer that degrades into acidic byproducts, into the matrix, for example, poly(glycolic acid-co-lactic acid) (PGLA). The PGLA degradation products lower the pH of the matrix, causing an interruption in the interactions and the subsequent release of the peptide. Control of the timing of the release can easily be done by the choice of the initial molecular weight of this fast degrading polymer, the copolymer ratio of lactic acid and glycolic acid within the PGLA polymer, and the choice of capping of the copolymer. Since all of these factors determine the kinetics of degradation, these factors can also be used to control the release of active agents from these devices. Other useful polymers producing pH-lowering (acidic) degradation products include poly(glycolic acid), poly(lactic acid), polycaprolactone, poly(hydroxyalkanoic acids) such as poly(hydroxybutyric acid) and poly(hydroxyvaleric acid), and the like.

It is important to note that the invention resides in the selection of a second polymer that is relatively more hydrophilic than the first polymer. Thus, when the first polymer is highly hydrophobic, a relatively less hydrophobic polymer may be used as the second polymer, even though it might otherwise ordinarily be considered hydrophobic as well. Likewise, when the second polymer is highly hydrophilic, a relatively less hydrophilic polymer may be used as the first polymer, even though it might otherwise ordinarily be considered hydrophilic as well. Thus, suitable compositions may be prepared using two polymers listed here as first polymers, or two polymers listed here as second polymers, provided that the first one hydrogen bonds with the active compound, and the second one is more hydrophilic than the first and degrades to form degradation products that promote the release of the biologically active compound from the first polymer. One of ordinary skill may even recognize combinations in which one of the first polymers functions as the second polymer and vice versa.

The compositions of the present invention are suitable for applications where localized drug delivery is desired, as well as in situations where systemic delivery is desired. Therapeutically effective dosages may be determined by either in vivo or in vitro methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the drug from the formulations of this invention are also varied within the routine skill in the art to determine an advantageous profile, depending on the therapeutic conditions to be treated.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

The compositions may be administered subcutaneously, intramuscularly, colonically, rectally, nasally, orally or intraperitoneally, employing a variety of dosage forms such as suppositories, implanted pellets or small cylinders, aerosols, oral dosage formulations and topical formulations, such as ointments, drops and transdermal patches. Liposomal delivery systems may also be used, such as small unilamellar vesicles, large unilamellar vesicles and multilamellar vesicles.

The following non-limiting examples set forth hereinbelow illustrate certain aspects of the invention. All parts and percentages are by weight unless otherwise noted and all temperatures are in degrees Celsius. The PAI peptide was obtained from COR Therapeutics of South San Francisco, Calif. Poly(DTH adipate) was prepared according to the procedure provided in Example No. 2 of U.S. Pat. No. 5,216,115. The polymer used had molecular weights ranging between 80-120 kDa. PEG was obtained from Aldrich Chemicals of Milwaukee, Wis. D,L-PLA and poly(s-caprolactone) were purchased from Medisorb and Aldrich, respectively. Both were of molecular weight 100 kDa. The drug and polymers were used without further purification. Solvents were of "HPLC grade" and were obtained from Fisher Scientific of Pittsburgh, Pa.

EXAMPLES

Figure 2:
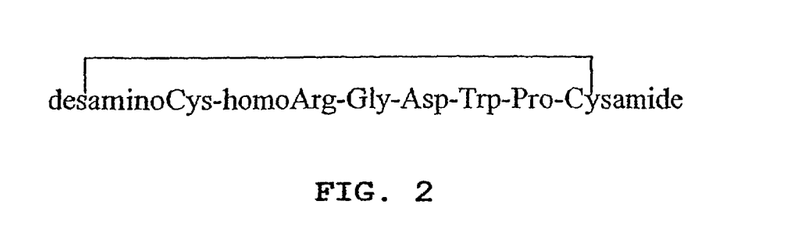
FIG. 2 depicts the amino acid sequence of INTEGRILIN™.

INTEGRILIN™ (antithrombotic injection) was chosen as the model peptide to explore the drug delivery applications of these materials (FIG. 2). This compound is a synthetic cyclic readily water soluble heptapeptide which is a highly potent glycoprotein IIb/IIIa antagonist. This compound has successfully demonstrated antithrombogenic behavior in vivo and devices fabricated by the formulation of this peptide into a polymer matrix with this property have many useful cardiovascular applications. In addition, this polymer contains an RGD sequence and therefore a device containing this peptide can find application as a component in scaffolds for tissue regeneration.

The blend of INTEGRILIN™ and poly(DTH adipate) was described in U.S. Pat. No. 5,877,224. There, it was mentioned that formulating films from these components using the coprecipitation melt-press technique resulted in specimens that released only trace amounts of peptide when incubated in PBS at 37° C. This was unexpected because the peptide is readily water soluble.

Fabrication of Release Devices

Compression molded films were fabricated from a coprecipitate containing 30% peptide and 70% polymer by weight. This co-precipitate was prepared by dissolving 0.15 g of peptide in 5 ml of methanol (HPLC grade) and 0.35 g polymer in 5 ml of methylene chloride (HPLC grade) and mixing the two solutions together to form a clear solution. This resultant solution was added drop-wise into 100 ml of stirred ethyl ether maintained at −78° C. White spongy precipitates were formed, filtered using a sintered glass filter, and dried under vacuum. After drying the co-precipitate was compression molded at 90° C. under a pressure of 5,000 psi. Films with a thickness of 0.1 mm (±0.02 mm) were obtained.

Device Characterization

Peptide loading was determined by dissolving 10.0 mg of a film in THF (HPLC grade) (1.0 ml) in a 10 ml volumetric flask and adding PBS (phosphate buffer saline) until the 10 ml line. The mixture was stirred for a minimum of 6 hours followed by HPLC analysis of the drug content in the aqueous medium. Methylene chloride replaced THF when characterizing samples composed of PLA or poly(s-caprolactone) due to their insolubility in THF.

Peptide Release Study

Films were cut into 0.5 cm² squares. The mean mass of the samples was 21 mg (±5). Each specimen was individually placed into 20 ml glass scintillation vials containing 10 ml of phosphate buffered saline (pH 7.4, 37° C.). The standard PBS solution used was composed of 10 mM phosphate buffer saline, 138 mM NaCl and 2.7 mM KCl. The buffer was changed at each time point and analyzed by HPLC for release of the peptide. There was a minimum of three samples per time point, each sample originating from a different film. The HPLC method involved a 3 cm C-18 Perkin Elmer cartridge column with a gradient mobile phase which began at 80% water/20% acetonitrile and ended with 75% water during a period of 5 minutes at a flow rate of 1 ml/min. Both the acetonitrile and water contained 0.1% (v/v) trifluoroacetic acid. The column was calibrated with known concentrations of the peptide dissolved in PBS to establish a calibration curve and the INTEGRILIN™ contained in the buffer of each sample was quantified using this curve. The HPLC pump used was a Perkin Elmer Series 410 LC pump and the detector used was a PE LC-235 diode array UV-VIS detector set at 280 nm. The data collected was analyzed using a PE Nelson 3000 Series Chromatography Data System.

At designated times, the samples were removed, rinsed with deionized water, blotted with a Kimwipe tissue and either placed in a vial for subsequent vacuum drying for mass retention and molecular weight retention studies or used for thermal gravimetric analysis (TGA) water uptake studies. Those devices that were not needed for gel permeation chromatography (GPC) or TGA studies were dissolved in organic solvent subsequent to drying and the peptide content extracted to ensure that all loaded peptide was accounted for.

Water Content Determination Using Thermogravimetric Analysis (TGA)

The quantity of water absorbed by the incubated samples was measured using a TGA 951 (TA Instruments, Inc.). The sample was removed from the buffer, rinsed in deionized water to remove buffer salts, and blotted dry with a Kimwipe tissue. A small sample (10 mg) was cut from the specimen and placed in an aluminum TGA pan. The sample was heated under a nitrogen flow at a rate of 10° C./min from room temperature to 225° C. The water uptake was measured by the loss in weight of the sample as it was heated from room temperature until 150° C.

Water Content Determination Using the Microbalance

At pre-determined time points, the samples were removed from the buffer, rinsed with deionized water and blotted dry. The sample's wet weight ($W_w$) was immediately taken using an electronic balance. The dry weight ($W_d$) was taken after the sample was dried under vacuum for at least two weeks, by this time constant weight was achieved. The amount of water uptake was calculated from the following equation:

$$\% \text{ Water uptake} = [(W_w - W_d)/W_d] \times 100$$

Differential scanning calorimetry analysis (DSC) to measure the melting point of the peptide and melt transitions in the polymer film DSC was used to determine the melting point of the peptide. A sample of approximately 2 mg of peptide was weighed out and sealed in a crimped aluminum DSC pan. The sample was heated at 12° C./min from room temperature to 200° C., under nitrogen flow. DSC was also used to determine whether there is a melting transition associated with the polymer films that contain 30% (w/w) peptide. A sample size of 6 mg of film was sealed in a crimped aluminum DSC pan and heated at 12° C./min until 200° C., under nitrogen flow. The melting point of the sample was determined by the temperature at which the sharp endotherm of melting occurred. All data was analyzed using the first-run thermogram. An empty aluminum pan was used as a reference in each experiment. The particular instrument used was a DS C 910 (TA instruments) and the instrument was calibrated with indium (m.p.=156.61° C.) before use.

Percent Mass Retention Study

The percent mass retention of the samples was calculated in the following manner. The sample was removed from the PBS incubation medium, rinsed in deionized water, and blotted with a Kimwipe tissue. It was placed in a fresh vial and dried under vacuum for 2 weeks. Following this dessication period, it was weighed ($W_d$). The mass obtained following incubation and drying was compared to the initial mass ($W_o$). The formula for calculating percent mass retention is the following:

$$\% \text{ Mass loss} = [(W_o - W_d)/W_o] \times 100$$

Molecular Weight Determination of the Polymers Using GPC

Film samples were dissolved in THF to obtain a concentration of 5 mg/ml and pre-filtered through a 25 um glass fiber filter and subsequently filtered through a 0.45 um PTFE filter prior to injection into the GPC. The molecular weights of the poly(DTH adipate) samples were calculated relative to a set of monodispersed polystyrene standards (Polymer Laboratories, Ltd. Church Station, U.K.) without further corrections. The GPC chromatographic system consisted of a Waters 510 HPLC pump, a Waters 410 differential refractometer detector, and a Digital Venturi's 466 PC running Millenium (Waters Corp.) software for data processing. Two PL-gel columns 30 cm in length (pore sizes of $10^3$ and $10^5$ A; Polymer Laboratories LTD, England) operated in series at a flow rate of 1 ml/min in THF. Samples composed of PLA or PCL were dissolved in methylene chloride instead of THF, but otherwise analyzed in the same way as the poly(DTH adipate) samples.

Formulation of Poly(DTH Adipate)/PLA Blend Films

Release devices composed of D,L-PLA and poly(DTH adipate) blends contained 30% (w/w) peptide. In the case of the 50/50 D,L-PLA/poly(DTH adipate), 0.15 g of INTEGRILIN™ was dissolved in 5 ml of methanol and 0.175 g of PLA and 0.175 g of poly(DTH adipate) were dissolved in 2.5 ml of methylene chloride, respectively. All the solutions were combined to form a clear solution. From this point the procedure for the fabrication of the poly(DTH adipate) devices was followed.

Devices composed of 75/25 PLA/poly(DTH adipate) were fabricated by dissolving 0.15 g of INTEGRILIN™ into 5 ml of methanol, 0.26 g of D,L-PLA in 4 ml of methylene chloride and 0.09 g of poly(DTH adipate) in 2 ml of methylene chloride and combining the three solutions. From this point the procedure for the fabrication of the poly(DTH adipate) devices was followed.

Fabrication and Incubation of Films Under Acidic Conditions

The same formulation protocol mentioned above was followed for these films, with the exception that concentrated HCl (12 molar) was added drop-wise to the stirred peptide/methanol solution until the pH, as measured by a pH meter dropped from 6.8 to 2.

The acidic media for the in vitro incubation studies conducted at pH of 2 was prepared in the following manner. Standard PBS solution was used and 12 M HCl was added drop-wise into the PBS until the PBS until the pH meter indicated that the desired pH had been obtained.

Incubation of Films Under Varying Ionic Strength Conditions

Three sets of films were prepared in the standard method mentioned above, one set was incubated in HPLC water, used as is. Another was incubated in the standard PBS buffer. The last set was incubated in PBS buffer that was twice the concentration of the standard PBS solution.

The Effect of the Peptide on the Glass Transition Temperature of Poly(DTH Adipate)

The glass transition temperature of sets of films was measured using Dynamic Mechanical Analysis (DMA). Measurements were performed on a DMA 983 from TA Instruments in a flexural bending deformation mode of strain. Each set of films contained a different weight percentage of peptide ranging from 0%-30% (w/w) of peptide. Samples of approximate size 5×10×1 mm were cut from the films and mounted on the instrument using low mass clamps, after calibrating the instrument with the low mass clamps. The samples were cooled using a liquid nitrogen cooling accessory to −30° C. and heated at a rate of 4° C./min until 70° C. The frequency was fixed at 1 Hz and the amplitude was 1 mm. The glass transition was read from the maxima of the E" peak.

Formulation of INTEGRILIN™/PLGA/Poly(DTH Adipate) Blend Films

Devices composed of INTEGRILIN™/PLGA/poly(DTH adipate) were prepared by the dissolution of 0.075 g of peptide in 2 ml of methanol, 0.21 g of PLGA in 3 ml of methylene chloride, and 0.21 g of poly(DTH adipate) in 3 ml of methylene chloride. The PLGA solution was pipetted into the poly(DTH adipate) solution. The INTEGRILIN™ solution was pipetted into the mixed polymer solution. The clear solution was added drop-wise into cold diethyl ether (−78° C.). The remainder of the procedure is the same as described above.

Characterization of Blend Films

The peptide loading of the film was determined as described above, using methylene chloride to dissolve the polymer matrix instead of THF.

Figure 21:
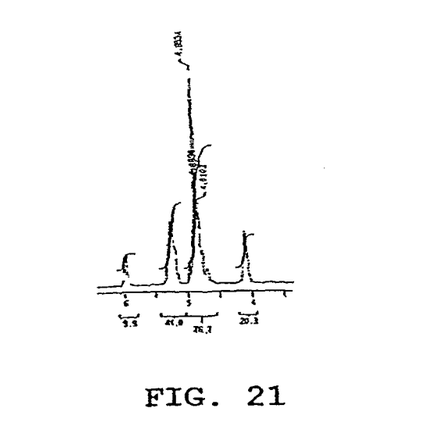
FIG. 21 depicts the NMR spectra of an INTEGRILIN™-containing PLGA/poly(DTH adipate) blend film.

The ratio of PLGA to poly(DTH adipate) in the polymer blend films was characterized using nuclear magnetic resonance (NMR)(FIG. 21). For each film, the ratio of the integration of the PGA methylene protons to that of the PLA methine proton was compared to the theoretical. It was determined that the experimental and theoretical ratios were within 10% of each other. Next, the integration of the PGA methylene protons (4.8 ppm) was compared to the integration of the methylene protons of the poly(DTH adipate) at 4.1 ppm. This peak at 4.1 ppm is associated with the protons on the methylene group that is next to the oxygen of the ester in the pendent chain. The theoretical ratio of these PGA protons to the above mentioned protons of poly(DTH adipate) is 3.86. All films were characterized in this manner and in all cases the error of the ratio of PGA to poly(DTH adipate) was within the error ratio of the PGA to the PLA.

For the NMR analysis 20 mg of the film was dissolved in 0.75 ml of deuterated chloroform. This solvent was chosen since the peptide is not soluble in it and it would therefore be transparent to the NMR, thereby preventing unnecessary complications of the spectra. The samples were analyzed using a Varian 200 MHz instrument. Integrations were made on the spectra after 256 acquisitions. Integrations on the samples were repeated 3 times to ensure accuracy, and values for the integrations were taken from the average of the three values.

Characterization of Film Surfaces of Using SEM

Following rinsing and drying under vacuum samples were attached to a SEM stub and sputter coated in a Balzers SCD 004 sputter coater with 7 rim of gold palladium. They were observed in an Amray 18301 SEM at 20 kV, magnification=90×.

Determination of Miscibility of Polymer Blends using DSC

A Thermal Analysis 2100 system incorporating a DSC 910 (TA Instruments, DE) was employed, and calibrated with indium (m.p. 156.61° C.) before use. A polymer with a known weight (4 mg) was sealed between two crimped aluminum pans. The sample was subjected to two consecutive heating scans in order to ensure an identical thermal history for all samples. In the first scan, the sample was heated at the rate of 10° C./min to 110° C. After the temperature was kept isothermal for 10 minutes, the sample was cooled to −20° C. using liquid nitrogen. This step erases the thermal history of the sample. The second scan was performed immediately thereafter at the rate of 10° C./min. The glass transition temperature was determined in the second scan as the midpoint of the endothermic step transition associated with the glass transition.

Formulation of INTEGRILIN™ with Poly(DTH Adipate)

Films composed of poly(DTH adipate) containing loadings of 5, 10, 15, 20, and 30% (w/w) peptide were prepared. Films containing even the highest loading were clear and flexible. In contrast, the films composed either of D,L-PLA or poly(E-caprolactone) (PCL) containing the same load of peptide were opaque and brittle. The clarity of the peptide/polyarylate films indicated that the phase separation in the case of the peptide and poly(DTH adipate) was sufficiently reduced that the separate polymer and peptide domains were too small to scatter light. This demonstrated an enhanced compatibility of peptide and tyrosine-derived polymer relative to blends of D,L-PLA and peptide or PCL and peptide.

The flexibility of the polyarylate films that contained peptide relative to those composed of the peptide and either of aliphatic polyesters can be explained by the lower glass transition temperature of the polyarylate (37° C.) as compared to that of PLA (52° C.), and the amorphous nature of the polyarylate as compared to PCL.

Release of Peptide from Films Incubated at 37° C. and at pH=7.4

Figure 3:
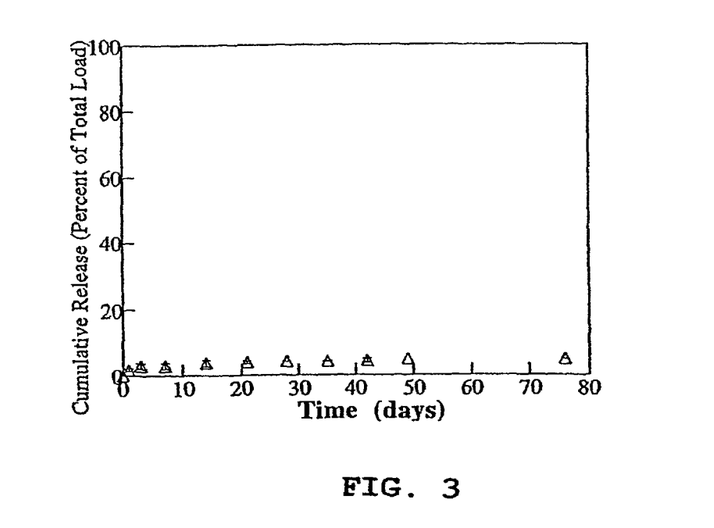
FIG. 3 depicts the release of INTEGRILIN™ from poly (DTH adipate) films containing 30% (w/w) peptide.
Figure 4:
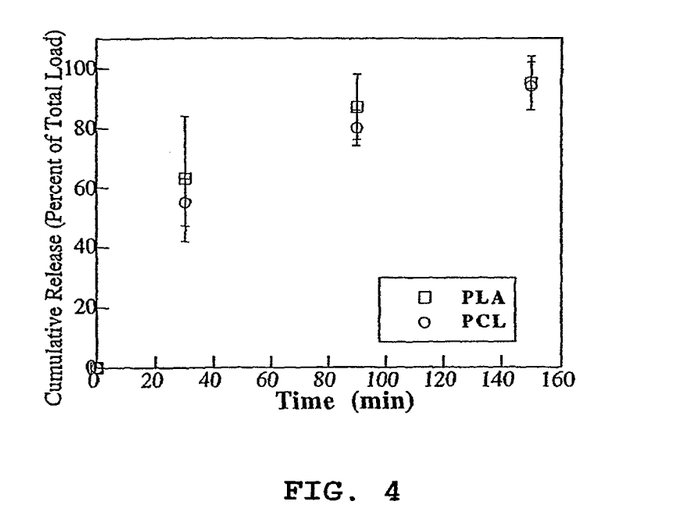
FIG. 4 depicts the release of INTEGRILIN™ from equivalent D,L-PLA and poly(E-caprolactone) films.

In this experiments the in vitro release behavior of the peptide, under simulated physiological conditions, from various polymer matrices was observed. Unexpectedly, both the aliphatic polymers released the peptide completely within three hours. In contrast, the poly(DTH adipate) demonstrated only trace release, over a period of 77 days, under the identical conditions (FIGS. 3 & 4).

Percent Mass Retention of Incubated Samples

Figure 5:
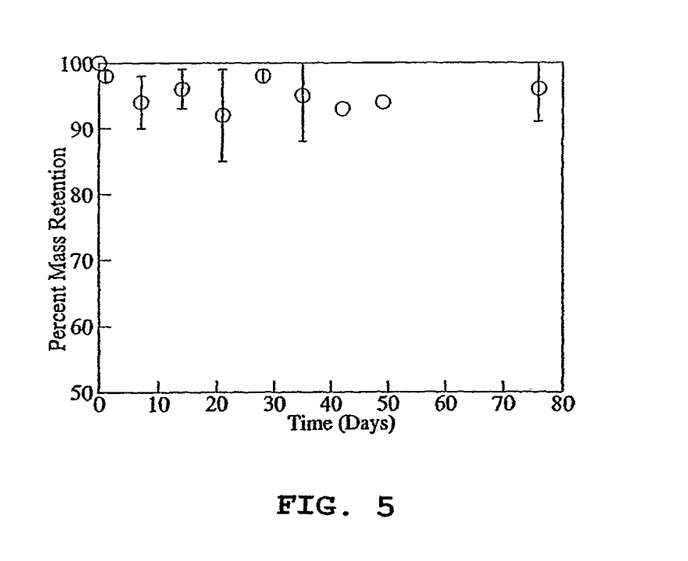
FIG. 5 depicts the percent mass retention of poly(DTH adipate) samples containing 30% (w/w) INTEGRILIN™.
Figure 6:
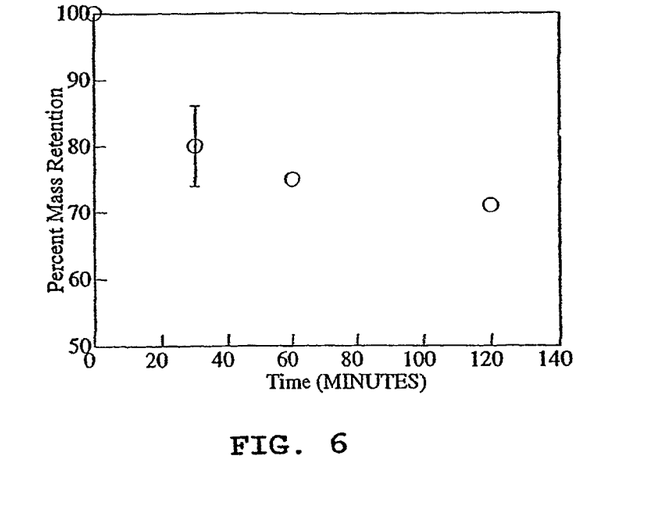
FIG. 6 depicts the percent mass retention from equivalent D,L-PLA films.

Poly(DTH adipate) samples containing 30% (w/w) peptide lost on average 5% mass during the 77 day incubation period (FIG. 5). In contrast, the D,L-PLA samples that were formulated in the identical fashion as the poly(DTH adipate) samples lost about 30% of their mass within two hours (FIG. 6). The results of these experiments, therefore, were consistent with the data obtained from the HPLC. In the case of the poly(DTH adipate) films containing 30% (w/w) peptide, the HPLC data indicate that these films released less than 10% of the loaded peptide (FIG. 3). This translates into a mass loss for the entire sample of about 3% over the 77 day period. This is in agreement with the average 50% mass loss observed for these samples.

In contrast to the poly(DTH adipate) samples that demonstrated minimal mass loss, the PLA samples showed extensive mass loss. These film samples also contained 30% (w/w)

peptide. HPLC data indicated that these samples released all of the peptide that they contained, which translates into a 30% mass loss over the three hour incubation period. The resulting percent mass retention data is about 70% for these samples is therefore in agreement with the HPLC results. Furthermore, since the peptide was released so rapidly by the PLA and PCL matrices, it can be concluded that the peptide is small enough to readily diffuse through the polymer chains and the development of pore structures and interconnecting channels is not necessary to release the molecules of peptide that are deep within the film. Therefore there should be minimal impedance for release of the peptide from the polyarylate.

Measurement of Water Absorption by Polymer Films during Incubation

Figure 7:
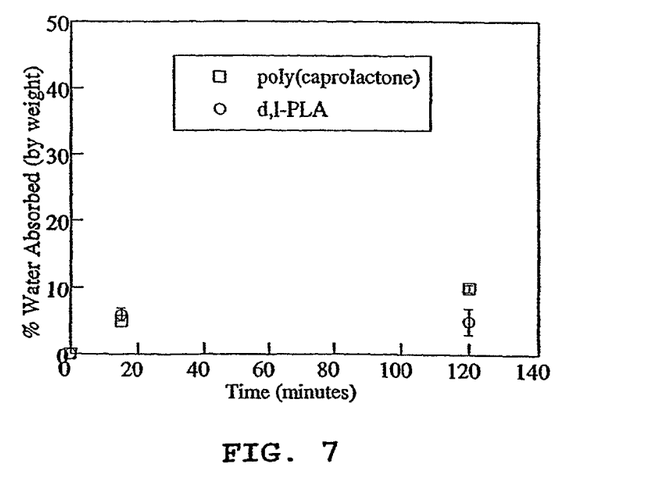
FIG. 7 depicts percent water absorption of PCL and PLA films containing 30% (w/w) INTEGRILIN™.
Figure 8:
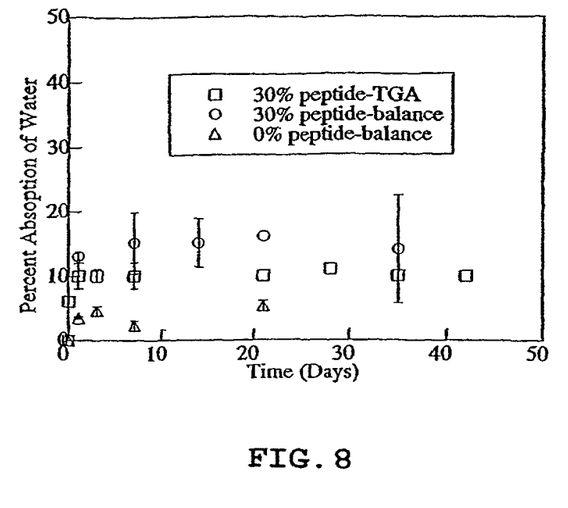
FIG. 8 depicts percent water absorption for an equivalent poly(DTH adipate) film.

Specimens of poly(DTH adipate) containing 30% (w/w) peptide absorbed about 10% by weight water within the first day and maintained that level of swelling throughout the entire incubation period. Also, the presence of the peptide increased the water absorption of the polymer from about 3% by weight to 10% by weight (FIG. 8). Samples of PLA and PCL containing identical loading of peptide to the poly(DTH adipate) also absorbed water within that range during the 2-3 hours that they were incubated (FIG. 7).

The similarity in water uptake between the three polymers when formulated in an identical manner with the peptide indicates that the absorption of water is not the determining factor for release of the peptide.

The Effect of the Peptide on the Molecular Weight of the Polymer

Figure 9:
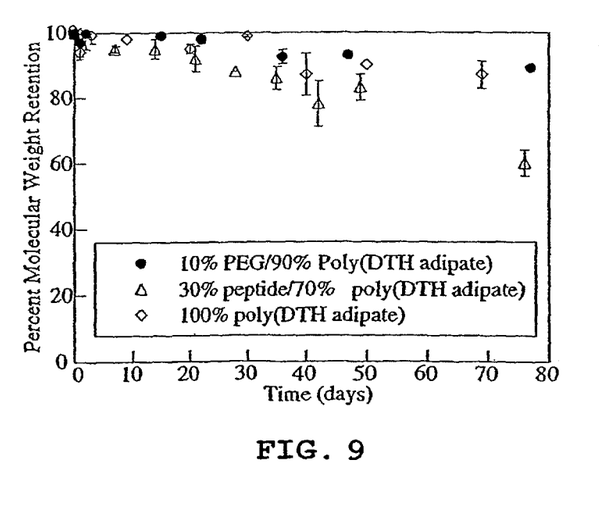
FIG. 9 depicts percent molecular weight retention of neat poly(DTH adipate) and poly(DTH adipate) containing 30% (w/w) INTEGRILIN™.

One of the amino acid residues on the peptide is an aspartic acid. Aspartic acid is a moiety that could introduce acidity into the polymer when the polymer is blended with the peptide. Consequently, an investigation of the molecular weight degradation of the polymer was made and compared to rate of degradation for the neat poly(DTH adipate) (FIG. 9).

As an additional control, samples composed of a blend of 10% (w/w) PEG and 90% (w/w) poly(DTH adipate) were included in these studies because these samples absorb 20% by weight water as measured by the TGA. This represents more water than is absorbed by the polymer samples containing 30% (w/w) peptide and this therefore can function as a control for the effect of the added water on the molecular weight degradation of the polymer. The results of these studies were that the samples containing peptide did degrade at a faster rate than the samples that did not contain peptide. After a period of over 2 months the poly(DTH adipate) samples containing 30% (w/w) peptide had undergone 40% molecular weight degradation. In contrast, those samples without peptide demonstrated almost no degradation during this time period.

In addition, the increased amount of water in the polymer matrix did not affect the rate of molecular degradation at all. There did not appear to be any significant difference in the rate of molecular weight degradation between the poly(DTH adipate) samples containing PEG and the neat samples. Therefore, it can be concluded that it was the presence of the peptide that had the catalytic effect on the degradation of the polymer. However, this increase in degradation rate was not significant enough to affect the release of the peptide.

Effect of Ionic Strength of the Medium on the Release of the Peptide

Figure 10:
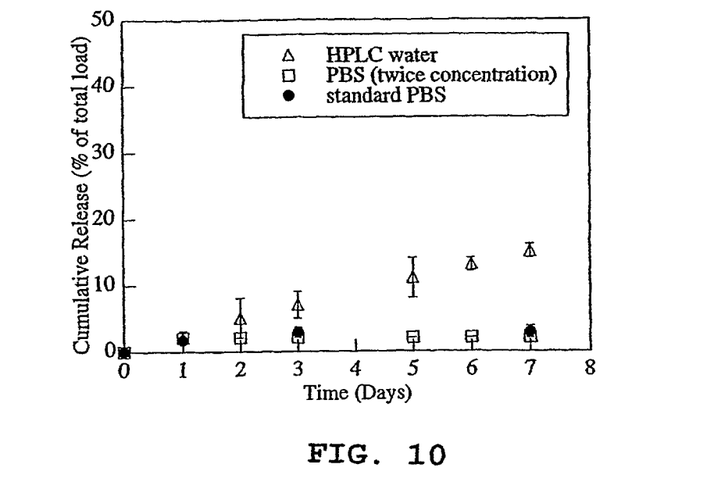
FIG. 10 depicts the effect of ionic strength on the release of INTEGRILIN™ (30% (w/w)) from poly(DTH adipate) films.

Poly(DTH adipate) films containing 30% (w/w) peptide were prepared in the standard manner. The pH of the incubation media remained about 7, but the ionic strength of the release media was varied. The in vitro release of the peptide in HPLC water, in the standard PBS solution (10 mM phosphate buffer saline, 138 mM NaCl, 2.7 mM KCl), and in PBS buffer formulated at twice the concentration (20 mM phosphate buffer saline, 276 mM NaCl, 5.4 mM KCl) was measured and compared (FIG. 10). It was observed that the rate of release of peptide was four times greater in HPLC water as compared to the release rate in phosphate buffer. These results demonstrate some hydrophobic interactions between the peptide and polymer, such as the pi stacking of the tryptophan ring of the peptide with the phenolic ring of the polymer.

Figure 11:
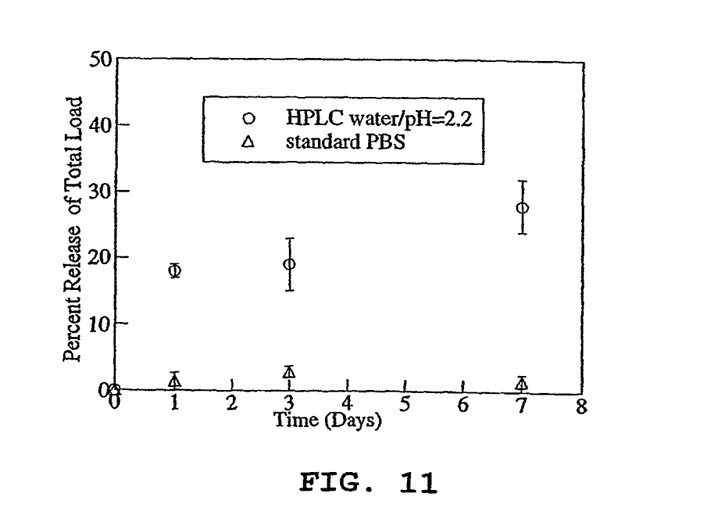
FIG. 11 depicts 30% (w/w) INTEGRILIN™ release from poly(DTH adipate) films at pH 2.2 without added electrolytes.

Incubation of Poly(DTH Adipate) Films Containing 30% (w/w) Peptide in Acidic and Low Ionic Strength Conditions Samples containing 30% (w/w) peptide were prepared under standard conditions and incubated in HPLC water containing 0.1% (v/v) trifluoroacetic acid, the pH of which was 2.2. The release rate of the peptide, when both pH and ionic strength of the incubation media were lowered was greater (FIG. 11) than when just one factor was lowered. When just the pH was lowered, 12% of the loaded peptide was released within three days. When just the ionic strength was reduced 8% of the loaded peptide was released within three days. When both parameters were lowered simultaneously 20% of the loaded peptide was released within this time period. Despite enhanced release in these conditions, the peptide was not "dumped out" as in the case of D,L-PLA but there was a continuous diffusion of the peptide from the poly(DTH adipate) matrix.

Figure 12:
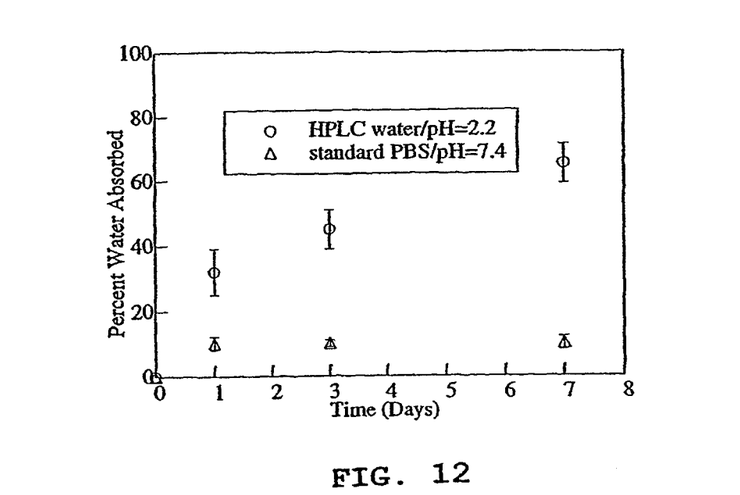
FIG. 12 depicts water uptake in 30% (w/w) INTEGRILIN™ poly(DTH adipate) films at pH 2.2 without added electrolytes.

However, what was unexpected was the absorption of water under these conditions (FIG. 12). Within the first day of incubation these samples swelled three times relative to the samples incubated in the standard PBS solution, and by the seventh day these samples swelled by seven times. From FIG. 9, it can be determined that the neat polymer, by itself, does not increase its absorption of water during this initial 7 day time period when incubated in the standard PBS solution. Moreover, since this polymer is relatively hydrophobic, it would not be expected that the change in incubation conditions would promote such an increase in the percentage of water uptake by the neat polymer. Therefore, it can be inferred that it is the peptide within the matrix that is the source of this large water uptake.

Therefore, incubation in the standard PBS solution favors the interaction of the peptide with poly(DTH adipate) rather than with water, hence, there was no increase in swelling beyond the initial 10% even over many weeks of incubation in these conditions. However, in conditions where the peptide-polymer interactions are weakened, as in this case, where both the pH and ionic strength of the incubation media were lowered, there is more of a driving force for the peptide to interact with water and consequently, there was a steady increase in the swelling of the film as more peptide molecules were exposed to and interacted with water.

Under these conditions of increased acidity and lowered ionic strength the film samples also turned opaque immediately. This opaqueness, noted only under the circumstances where there was enhanced release of the peptide from the poly(DTH adipate) films, appears to be correlated with increased water absorption by the film samples. The weakening of the intensity of the peptide-polymer interactions result in an increase in water absorption and the developing opacity, is caused by the water that occupies the free volume within the polymer matrix.

The absorption of 10% by weight water was sufficient to release the peptide to completion in the case of the aliphatic polymers. However, samples whose matrix was composed of poly(DTH adipate) instead of PLA, absorbed 70% by weight water and yet did not release the peptide in the same "dumping" manner that the PLA and PCL matrices did at 10% by weight of water absorption.

The interaction of the peptide with the tyrosine-derived polyarylate arises from the unique structure of the polymer in which the amide bond of each repeat unit is in close proximity to the pendent ester in the same unit. This entire region can be considered as one functional group, the amidocarboxylate group, and can act as a pocket for the hydrogen bonding of various groups on the peptide.

Peptide-Polymer Interactions with Other Tyrosine-Derived Polymers

Several other polymers were screened for the diffusion of the peptide. The loadings of peptide used in these screening experiment were lower than those used with poly(DTH adipate), but they were sufficient to expect release of this readily water-soluble peptide barring any interactions to impede it.

Figure 13:
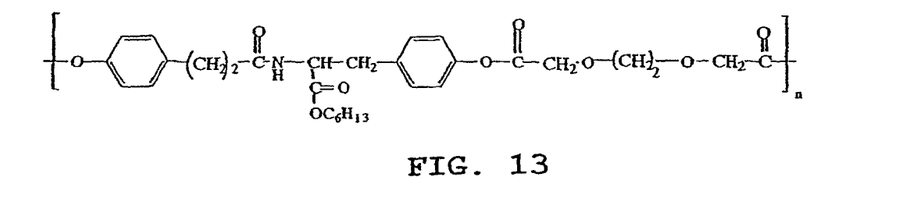
FIG. 13 depicts the structure of poly(DTH dioxaoctanedioate)

Poly(DTH dioxaoctanedioate) was the first alternate but structurally related polymer investigated. This polymer contains the DTH repeat unit, which makes it similar to poly (DTH adipate). However, this polymer is synthesized by polymerizing DTH with dioxaoctanedioic acid (FIG. 13) instead of adipic acid.

Figure 14:
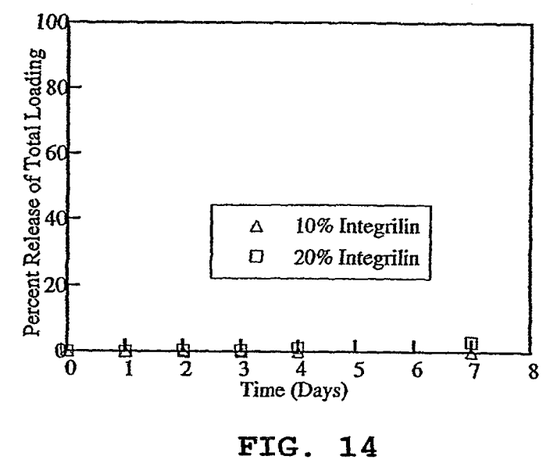
FIG. 14 depicts the release of INTEGRILIN™ from poly (DTH dioxaoctanedioate) films.

No peptide was released from these films (FIG. 14) indicating that increasing the hydrophilicity of the polymer does not have an effect on the release of the peptide. The water uptake of the films was also measured and found to be 5% by weight in the case of films that contained 10% (w/w) peptide and 10% by weight in the case of films containing 20% (w/w) peptide. This indicates that although the loading of the peptide is lower in these specimens there is the same amount of water in bulk in poly(DTH adipate) specimens containing 30% (w/w) peptide as in poly(DTH dioxaoctanedioate) containing 20% (w/w) peptide. In addition, the structure of this polymer differs from poly(DTH adipate) only in the structure of the flexible backbone unit. Since the release behavior of this polymer is similar to that of poly(DTH adipate), and the structural differences between the two polymers lie only in the structure of the backbone unit, it can be concluded that the DTH unit is what is most integral to the peptide-polymer interactions.

Figure 15:
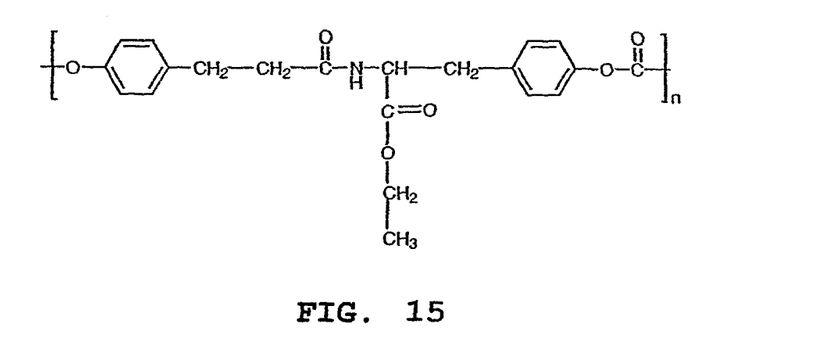
FIG. 15 depicts the structure of poly(DTE carbonate)

Another polymer structure was substituted for poly(DTH adipate), poly(DTE$_{0.95}$-co-PEG$_{(1000)0.05}$ carbonate). This polymer is a random copolymer of desaminotyrosyl tyrosine ethyl ester (DTE) and poly(ethylene glycol) (PEG) (FIG. 15) and shares the basic desaminotyrosyl tyrosine alkyl ester repeat unit with the poly(DTH adipate), but contains carbonate linkages and not ester in the backbone, and no diacid component. The absence of the diacid component and the similarity in the tyrosine-derived repeat unit should further confirm that it is the tyrosine-derived component and not the diacid that is involved in these interactions should the peptide fail to diffuse from this polymer. Films containing 10% (w/w) peptide were prepared.

Figure 16:
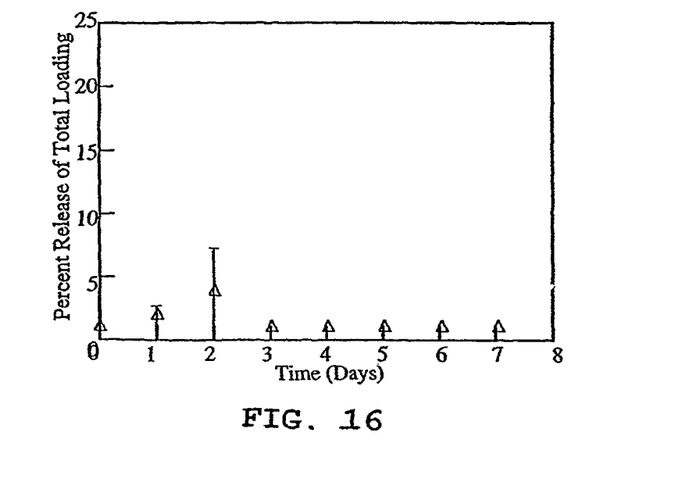
FIG. 16 depicts the release of 10% (w/w) INTEGRILIN™ from poly(DTEcoPEG)

Peptide release from these polymers also was minimal (FIG. 16). The water uptake of these samples was also measured, and during the period of incubation the film samples absorbed 10% by weight water. Again, this is the same amount of water absorbed by the PLA, PCL, and poly(DTH adipate) samples. Although the peptide loading is lower in these films it is not surprising that the water uptake is as much as samples of these other polymer systems since the PEG increases the hydrophilicity of these samples. These data demonstrate that the minimal release of the peptide from polymers containing the DTR unit is the result of the tyrosine-derived repeat unit being the structure responsible for the absence of diffusion of the peptide from the polymer.

Figure 17:
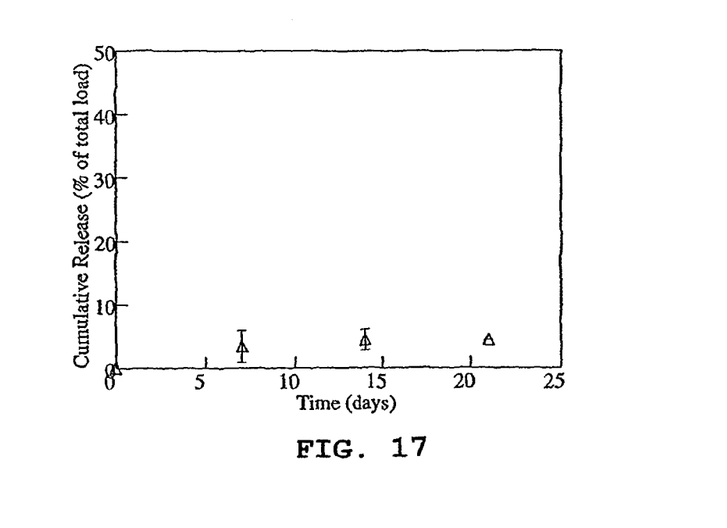
FIG. 17 depicts the release of 15% (w/w) INTEGRILIN™ from poly(DTE carbonate)

Poly(DTE carbonate) was also formulated with 15% (w/w) peptide. This polymer structure contains only the desamino-tyrosyltyrosine ethyl ester with carbonate linkages and does not contain any PEG. These films also showed the same behavior as the tyrosine-derived polyarylates (FIG. 17). The water uptake of these films was also measured and found to be 6% by weight over the incubation period.

In Vitro Release of the Peptide from Poly(DTH Adipate)/D, L-PLA Blends

Figure 18:
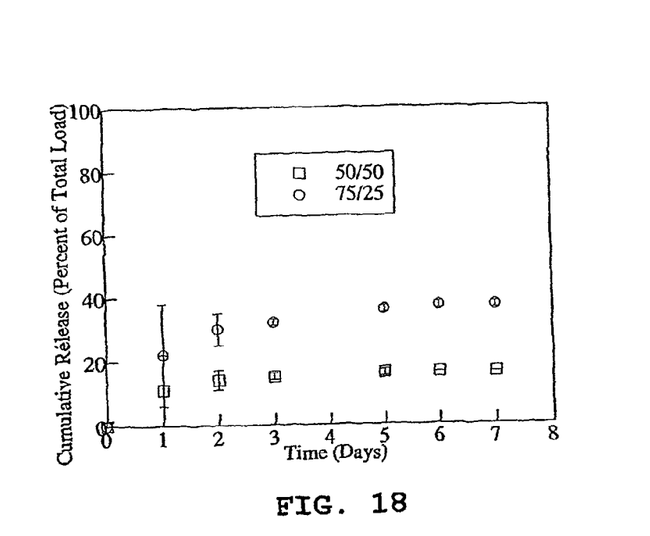
FIG. 18 depicts in vitro release of 30% (w/w) INTEGRILIN™ in PBS (pH=7.4, 37° C.) from D,L-PLA/poly(DTH adipate) films.

The in vitro release study of the peptide from poly(DTH adipate) resulted in about 5% release of the loaded peptide. Release of the peptide from D,L-PLA matrices under the same conditions resulted in the complete release of the loaded peptide within three hours. In vitro release studies of the peptide from the D,L-PLA/poly(DTH adipate) blend films resulted in a moderate burst and an extended release of the peptide relative to release from D,L-PLA (FIG. 18). Those samples with a 1:1 ratio of poly(DTH adipate) to D,L-PLA released 18% of the total peptide load within five days. Those samples containing a 3:1 ratio of D,L-PLA to poly(DTH adipate) released 40% of the peptide load within five days. In both formulations, therefore, the initial burst of peptide was reduced relative to the burst from the D,L-PLA films. Moreover, the release was extended from the original three hours associated with the D,L-PLA matrices.

Pulsatile Delivery of a Model Water Soluble Peptide: Preparation of Films Composed of Peptide, PLGA, and Poly(DTH Adipate)

TABLE 1

Characteristics of PLGA in each film set

| | Film Set | | |
|---|---|---|---|
| | I | II | III |
| M$_w$, (kilodaltons) | 12 | 25 | 62 |
| Polydispersity | 2.4 | 3.4 | 2.0 |
| T$_g$ (° C.) | 39.5 | 45.3 | 48.2 |
| PLA:PGA (mole ratio) | 53:47 | 52:48 | 54:46 |

Figure 19:
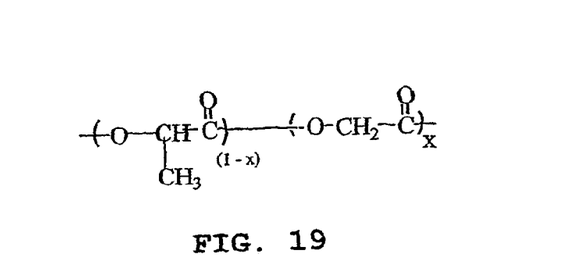
FIG. 19 depicts the chemical structure of PLGA.

PLGA is a resorbable copolymer composed of poly(lactic acid) and poly(glycolic acid) that is known to release acidic compounds during the degradation process (FIG. 19). Three sets of blend films were prepared. All films contained 15% (±2) (w/w) peptide, 42% (w/w) uncapped PLGA, and 43% poly(DTH adipate). They only differed in the molecular weight of PLGA that they contained (Table 1).

Visual Inspection of Blend Films

In contrast to the transparent nature of the peptide/poly (DTH adipate) films, these films appeared homogeneously opaque, very similar to the blends composed of peptide, D,L-PLA and poly(DTH adipate) described previously, suggesting increased phase separation of the peptide/PLGA/poly (DTH adipate) relative to the peptide/poly(DTH adiapte) films. In addition, these films were less flexible as compared to films made without PLGA. As expected, the brittleness increased with decreasing molecular weight of PLGA.

Differential Scanning Calorimetry of Blend Films

Two glass transition temperatures were evident on the thermograms of all films containing the blend of PLGA and poly(DTH adipate) confirming the phase separation present in these blend films. The lower T$_g$ occurring at about 34° C. is associated with the poly(DTH adipate) domains. The higher one at 49° C. corresponds to the PLGA domains. The appearance of the two glass transitions signifies that the two polymers are immiscible and therefore, there are separate domains of PLGA and poly(DTH adipate) present in the films.

It was also noted in samples that were heated to 200° C. that there was no endotherm in the corresponding thermogram, characteristic of the neat peptide, indicating that in these matrices, too, the peptide is not present in discrete crystalline domains.

Release of the Peptide from Poly(DTH Adipate)/PLGA Blend Film Matrices

Figure 20:
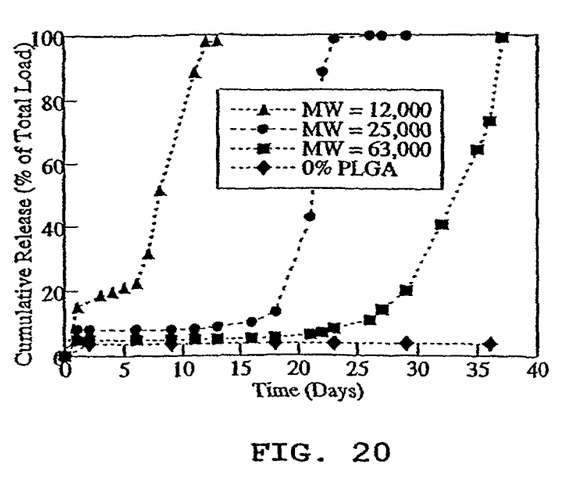
FIG. 20 depicts the cumulative release of 15°/0 (w/w) INTEGRILIN™ from a 50:50 blend of poly(DTH adipate) and PLGA.

Film samples of the PLGA and poly(DTH adipate) blends were incubated in PBS at 37° C. (FIG. 20). As expected, there was a small burst. The size of this burst appears to be related to the molecular weight of the PLGA. In general, samples containing the lowest molecular weights of PLGA were associated with larger bursts (11%-18% of loaded peptide) than samples containing the highest molecular weight of PLGA (6% of the loaded peptide). However, no sample released more than 20% (w/w) of the loaded peptide in this fashion. The source of this correlation between decreasing molecular weight and burst, perhaps, is that the lower molecular weight polymer is more hydrophilic than the higher molecular weight polymer, due to the larger number of endgroups present in the lower molecular weight polymers as compared to higher molecular weight polymers. Therefore, the lower molecular weight polymers have more of an affinity for the peptide. As the molecular weight increases, the hydrophilicity decreases, resulting in a smaller initial release.

The lag time between release phases also displayed a direct relation with the initial molecular weight of the PLGA. There was a lag time of less than 5 days associated with the films containing the lowest molecular weight of PLGA. Furthermore, the release of the peptide following the lag phase was quite rapid. The entire load of peptide was released by twelve days, and the majority within about four days.

Samples containing PLGA of molecular weight 25 kDa displayed a lag time that varied from 18 to 26 days (the majority of the samples exhibited a delay time of approximately 18 days, and only one sample displayed a 26 day lag time). The release of peptide after the lag phase was also quite rapid and the entire load of peptide was released within about 5 days.

Samples containing the highest molecular weight PLGA (63 kDa) showed a lag time that varied from 27 to 34 days, with most of the samples concentrated around the 27 day mark. After the lag time the release was rapid, but not as rapid as samples with lower molecular weight PLGA. These samples released their load of peptide over a period of about 10 days.

During the lag periods, less than 2% of the loaded peptide was leached out from the blend films. This signifies that although this formulation does not contain a true barrier but relies only on peptide-polymer interactions to prevent release of the peptide during the delay phase, this system works just as well as a barrier technique. As a control, samples of poly(DTH adipate) containing 15% (w/w) peptide but no PLGA were formulated. These samples released almost no peptide during the incubation period.

The time required for the PLGA to degrade sufficiently to form the acidic byproducts controls the length of lag time. Samples with lower initial molecular weight of the PLGA require a shorter length of time to reach the critical degradation phase. Therefore, those samples with the lowest molecular weight of PLGA were associated with the shortest lag times and those with the largest initial molecular weight corresponded to the longest lag time before release. The samples containing the largest initial molecular weight of PLGA also displayed the slowest rate of release following the lag time. Although there is a sufficient concentration of acid products in the matrix of the polymer to release the peptide, the concentration did not quite reach the same level as that of the samples from polymers with lower initial molecular weights. Therefore, the effect of weakening the interactions is less intense resulting in a slower release of the peptide Monitoring the pH of the Incubation Media During the in vitro peptide release experiment the pH of the incubation media was monitored at each time point during the buffer change. As a control, a poly(DTH adipate) film containing 15% (w/w) INTEGRILIN™ was incubated and its pH measured, as well.

Samples of $PLGA_{12,000}$ maintained a pH of 7.4 for 9 days. Following this period the pH of the buffers of these samples steadily fell and by the end of the incubation period the pH of the buffers had reached 7.0. The sharpest decline in pH exactly mirrored the sharpest increase in release of the peptide.

The pH of the buffers of the samples of $PLGA_{25,000}$ measured 7.4 for the first 15 days of incubation. Following this period the pH of the buffer was 7.2 and this pH was maintained until 21 days when the buffer reached its lowest pH of 6.9. For the remainder of the incubation period the pH of the buffer vacillated between 7.0 and 7.2.

The pH of the buffers of the samples containing the highest molecular weight PLGA, maintained physiological pH until the $32^{nd}$ day. At this point the pH dropped to 7.0 and for the remainder of the incubation period the pH of the buffer vacillated between 7.0 and 7.3.

The coinciding of the drop in the pH of the buffer with the release of the peptide occurred because during the incubation of the samples the PLGA phase in the films began the molecular weight degradation process, and the acidic degradation products accumulated within the bulk of the matrix. Eventually a critical acid concentration was reached and the peptide-polymer interactions were weakened, resulting in the release of the peptide. However, the water-soluble degradation products also diffuse out of the matrix, so there is a codiffusion of the peptide with the acidic degradation products. Because of this codiffusion effect, the drop in pH of the buffer either coincides with the release of the peptide or occurs within a short time after the release of the peptide has begun.

Percent Mass Retention of Blend Films.

The samples composed of peptide, PLGA, and poly(DTH adipate) blends were rinsed after incubation, dried, and weighed after drying. The percent mass retention of these samples all ranged between 60 and 70% (Table 2). If only the peptide was released the percent mass retention would be approximately 85%. The fact that the mass loss was greater than 15% suggests that some degradation occurred. Since the films containing just peptide and poly(DTH adipate) did not show significant mass loss, the component lost from these blends was PLGA which degrades into water soluble oligomers.

Percent Mass Retention of Blend Films

TABLE 2

Percent mass retention of film samples containing a PLGA - poly(DTH adipate) blend

| MW of PLGA in film set | Percent Mass Retention | Days Incubated |
|---|---|---|
| 12 kda | 70 ± 3 | 12 |
| 25 kda | 60 ± 4 | 35 |
| 62 kda | 62 ± 4 | 50 |
| No PLGA | 99 ± 0.2 | 44 |

The molecular weight of the poly(DTH adipate) in these blend samples was also investigated. After drying, film samples were analyzed, using GPC, for their molecular weight. As a control, poly(DTH adipate) films containing 15% (w/w) peptide were also incubated in PBS and the percent molecular weight retention was compared to those samples that contained PLGA. To calculate the percent molecular weight retention, the molecular weights of the films after incubation were normalized to the molecular weight of the virgin poly(DTH adipate) (100 kDa) that was used to prepare the films. The virgin polymer was used and not the molecular weight of the films before incubation as would normally be done because the blended PLGA can dramatically alter the true value for the molecular weight of poly(DTH adipate) by artificially raising the proportion of low molecular weight fractions.

The effect is more dramatic before the films are incubated than after since during incubation the PLGA is reduced to oligomers and the molecular weight data represented by the main peak in the GPC trace of the film after incubation, for the most part, does not include the molecular weight of PLGA or includes a reduced fraction of PLGA as compared to before incubation. Consequently, by normalizing the data to the virgin polymer the change in molecular weight of poly(DTH adipate) during incubation is followed and not the change in molecular weight of the PLGA blend (Table 3).

TABLE 3

Percent Mw Retention following poly(DTH adipate) incubation in PLGA film samples c

| PLGA Mw in film set | Percent Molecular Weight Retention of poly(DTH adipate) | Days Incubated |
|---|---|---|
| 12 kda | 53 ± 12 | 16 |
| 25 kda | 47 ± 5 | 38 |
| 62 kda | 40 ± 3 | 47 |
| No PLGA | 52 ± 1 | 45 |

No correlation between the percent molecular weight retention of the blend films and release of the peptide was observed (Table 3). The sample sets containing the two lower molecular weight polymers of PLGA degraded to the same extent as the control film containing no PLGA. However, the films containing PLGA released the peptide and the control did not. Therefore, a massive degradation of poly(DTH adipate) did not occur. This is not the mechanism responsible for the release of the peptide Scanning Electron Microscopy (SEM) of Blend Film Surfaces Following Incubation Changes in surface morphology during incubation of poly (DTH adipate)/PLGA$_{12,000}$ films containing 15% (w/w) peptide were investigated using SEM. A comparison of surface morphology before and after incubation showed that the surface, originally, was relatively smooth, although quite porous. After an incubation period of 16 days, the surface became much rougher eliminating any resemblance to the smoothness that was observed before incubation. In addition, large cracks and holes developed. These pores, holes and cracks are PLGA-rich domains that are now empty due to the degradation of the PLGA and the subsequent dissolution of the water-soluble degradation products. These domains do not represent peptide-rich domains, because such phase separation would have led to a fast and immediate release of the peptide and not this delayed response.

The surface of control samples composed of 15% (w/w) peptide and 85% (w/w) poly(DTH adipate), in contrast, did not appear to change significantly over the same 16 day incubation period. This further confirms that these samples did not undergo the same dramatic changes that the samples containing PLGA did.

The polymer blends of the present invention thus provide formulations for the pulsatile release of biologically active compounds in which the active compound is "locked" by means of hydrogen bonding in a relatively hydrophobic polymer matrix until such time as the less hydrophobic polymer of the blend hydrolytically degrades to promote the release of the active compound from the more hydrophobic polymer. The length of delay and the rate of delivery following the delay can be reproducibly controlled through the selection of materials and the quantities employed.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not to be regarded as a departure from the spirit and scope of the invention, and all such modifications are intended to be included within the scope of the following claims.

What is claimed is:

1. A formulation comprising:
    a biologically active compound having a chemical structure with hydrogen bonding sites,
    a first biocompatible, hydrolytically degrading polycarbonate comprising hydrogen bonding sites and desaminotyrosyl-tyrosine diphenol monomer units, and
    a second biocompatible, hydrolytically degrading polymer that is less hydrophobic than said polycarbonate, wherein said second polymer degrades hydrolytically to form acidic degradation products that promote the release of said active compound, and wherein said second polymer is selected from the group consisting of a poly(glycolic acid), a poly(lactic acid), a poly(glycolic acid-co-lactic acid) (PGLA), a polycaprolactone and a poly(hydroxyalkanoic acid).

2. The formulation of claim 1, wherein said biologically active compound is pharmaceutically active.

3. The formulation of claim 2, wherein said pharmaceutically active compound is a peptide.

4. The formulation of claim 3, wherein said peptide is a cyclic peptide.

5. The formulation of claim 4, wherein said peptide is a platelet aggregation inhibiting (PAI) peptide.

6. The formulation of claim 5, wherein said PAI peptide is a synthetic cyclic heptapeptide antagonist of glycoprotein IIb/IIIa.

7. The formulation of claim 1, wherein said desaminotyrosyl-tyrosine diphenol monomer units comprise desaminotyrosyl-tyrosine esters.

8. The formulation of claim 7, wherein said esters are an ethyl or hexyl ester.

9. The formulation of claim 1, wherein said second polymer is PGLA.

10. A formulation comprising:
    a biologically active compound having a chemical structure with hydrogen bonding sites,
    a first biocompatible, hydrolytically degrading polycarbonate comprising hydrogen bonding sites, desaminotyrosyl-tyrosine diphenol monomer units, and randomly block copolymerized with poly(alkylene oxide), and
    a second biocompatible, hydrolytically degrading polymer that is less hydrophobic than said polycarbonate, wherein said second polymer degrades hydrolytically to form acidic degradation products that promote the release of said active compound, wherein said second polymer is selected from the group consisting of a poly(glycolic acid), a poly(lactic acid), a poly(glycolic acid-co-lactic acid) (PGLA), a polycaprolactone and a poly(hydroxyalkanoic acid).

11. The formulation of claim 10, wherein said biologically active compound is a cyclic peptide.

12. The formulation of claim 10, wherein said desaminotyrosyl-tyrosine diphenol monomer units comprise desaminotyrosyl-tyrosine esters.

13. A method for the pulsatile delivery of an active compound to a patient in need thereof comprising administering to said patient a formulation comprising:

a biologically active compound having a chemical structure with hydrogen bonding sites, a first biocompatible, hydrolytically degrading polycarbonate comprising hydrogen bonding sites and desaminotyrosyl-tyrosine diphenol monomer units, and a second biocompatible, hydrolytically degrading polymer that is less hydrophobic than said polycarbonate, wherein said second polymer degrades hydrolytically to form acidic degradation products that promote the release of said active compound, and wherein said second polymer is selected from the group consisting of a poly(glycolic acid), a poly(lactic acid), a poly(glycolic acid-co-lactic acid) (PGLA), a polycaprolactone and a poly(hydroxyalkanoic acid).

14. The method of claim 13, wherein said biologically active compound is a cyclic peptide.

15. The method of claim 13, wherein said polycarbonate is randomly block copolymerized with a poly(alkylene oxide).

* * * * *